United States Patent [19]

Trost et al.

[11] 4,051,157

[45] Sept. 27, 1977

[54] CATALYTIC ALLYLIC ALKYLATION

[75] Inventors: Barry M. Trost; Thomas R. Verhoeven, both of Madison, Wis.

[73] Assignee: Wisconsin Alumni Research Foundation, Madison, Wis.

[21] Appl. No.: 646,640

[22] Filed: Jan. 5, 1976

[51] Int. Cl.$^2$ .............................................. C07J 9/00
[52] U.S. Cl. ................... 260/397.1; 560/127; 560/125
[58] Field of Search ............... 260/397.1, 468 L, 397

[56] References Cited

U.S. PATENT DOCUMENTS 3,793,350  2/1974  Crabbe .......................... 260/397.45

*Primary Examiner*—Elbert L. Roberts
*Attorney, Agent, or Firm*—McDougall, Hersh & Scott

[57] ABSTRACT

Allylic alkylation with retention of configuration of a substrate having an allylic carbon-oxygen bond by reaction with a nucleophile in the presence of a Pd° with an excess of a phosphine.

15 Claims, No Drawings

CATALYTIC ALLYLIC ALKYLATION

The Government has rights in this invention pursuant to Grant No. NSF MPS-71-03396 and IPA No. 0001 awarded by the National Science Foundation, and Grant No. NIH 5-RO1-GM-13598 awarded by the Department of Health, Education, and Welfare.

This invention relates to allylic alkylation with stereochemical control for retention of configuration.

Control of stereochemistry in acyclic systems has been a formidable problem in synthetic organic chemistry. A classic example is creation of stereochemistry at C-20 of steroids.

This application is addressed in the discovery that an allylic carbon-oxygen bond (alcohol, ether, or ester) can be replaced with a nucleophile, with retention of configuration when the reaction is carried out in the presence of a palladium catalyst.

The allylic carbon-oxygen bond is one where the carbon is alpha to a double bond and connects to an oxygen group in the form of an alcohol, ether, or ester. Under these conditions, the reaction is completely stereospecific and is applicable generally to any allylic system of the type described, as illustrated by the following:

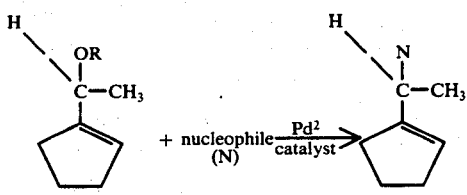

RO— = hydroxy
RO— = ether
RO— = ester or

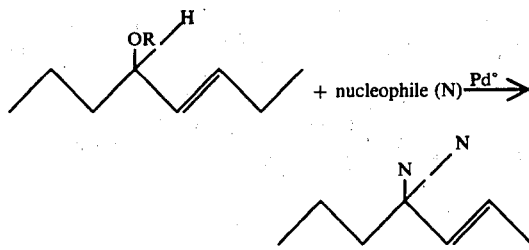

or

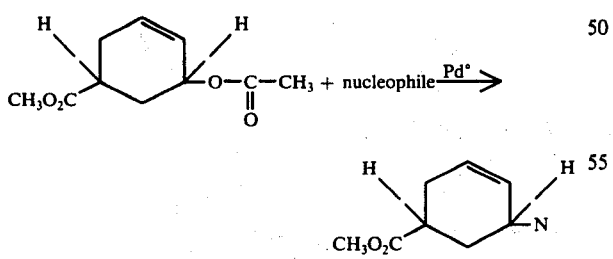

The concept that is important in the practice of this invention resides in the ability to achieve stereochemical control which enables substitution for a carbon-oxygen bond with retention of configuration. Ordinarily substitution results in inversion and it was wholly unexpected to obtain substitution with retention of configuration, which results from two conversions.

The invention will hereinafter be described with reference to the following examples which are given by way of illustration, and not by way of limitation of reactions which are typical of the practice of this invention.

EXAMPLE 1 alkylation of 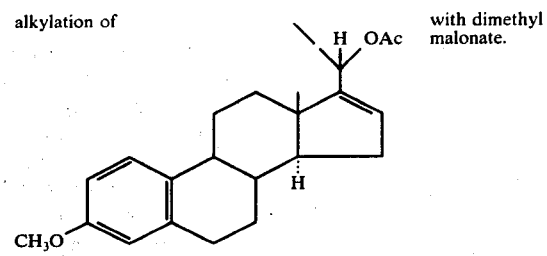 with dimethyl malonate.

The allylic acetate (1) (180 mg, 0.058 m mol), triphenylphosphine (9.32 mg. 0.0356 m mol) and tetrakistriphenylphosphine palladium (0) (4.1 mg, 0.00356 m mol) are stirred under argon in 5 ml of degassed tetrahydrofurane (THF) (distilled from sodium benzophenone ketyl) for 20 minutes. Dimethyl sodiomalonate, in 5 ml of THF, [prepared from 440 mg (3.34 m mol) of dimethyl malonate and 80.3 mg (3.34 m mol) of sodium hydride] was added in one portion to the above and the resulting mixture refluxed for 20 hours. The reaction was partitioned between ether and water, extracted with 4 aliquots of 30 ml each of ether, dried over magnesium sulfate, and evaporated in vacuo to give a yellow oil. Purification by plc (silica gel PF 254, hexane:ethyl acetate 2.5:1) gave 180.1 mg (83% yield) of an oil identified as the desired alkylated product (2).

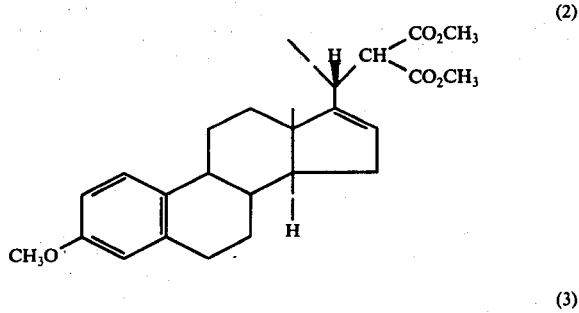

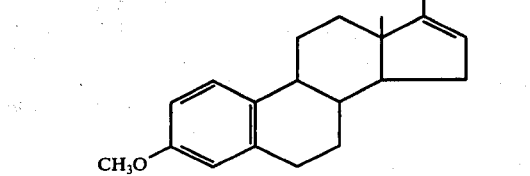

Decarbomethoxylation and hydrolysis to the acid (3) gave a crystalline solid, mp 162.5°–164.0°. IR 3650–2600 and 1710 cm$^{-1}$ (CO$_2$H), 1606 (C=C), 1570 and 1500 (aryl). NMR δ0.98, bs, 1H; 7.16, bd, J = 8 Hz, 1H; 6.10 m, 2H; 5.42, m, 1H; 3.80, s, 3H; 1.10-2.95, m, 16H; 1,12, d, J = 8 Hz, 3H; 0.81, s, 3H.

EXAMPLE 2

Allylic alkylation of Cis-3-Acetoxy-5-carbomethoxycyclohex-1-ene

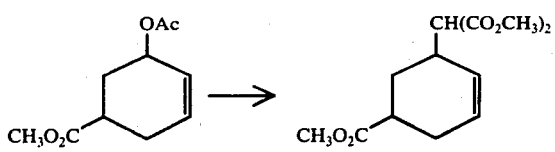

The allylic acetate (4) (50 mg. 0.252 m mol) was dissolved in 1.2 ml of dry degassed tetrahydrofurane (THF) and 8.4 mg (0.00738 m mol) of tetrakistriphenyl phosphine palladium (0) and 32.8 mg (0.123 m mol) of triphenyl phosphine was added. After stirring the clear yellow solution for 15 minutes, a solution of dimethyl sodiomalonate in 3 ml of dry THF [prepared from 166 mg (1.26 m mol) of dimethyl malonate and 32.2 mg (1.26 m mol) of sodium hydride] was added in one portion. After refluxing for 10 hours, the reaction was worked up as in Example 1. Purification of the product by plc (silica gel PF 254, hexand;ethyl acetate 5:1) gave 56.8 mg (83% yield) of colorless oil having the structure of formula (5). IR 1760 an 1740 cm$^{-1}$. NMR $\delta$5.4–5.8, $m$, 2H; 3.73, $s$, 6H; 3.63, $s$, 3H; 3.12, $d$, $J = 9$ Hz, 1H; 2.88, $m$ 1H; 2.48, $m$, 1H; 2.1, $m$, 2H; 1.34, $m$, 2H.

Palladium at a neutral oxidation level (Pd°), corresponding to metallic palladium in a very active state, is the preferred catalyst. It can be generated in a known manner and isolated for introduction into the reaction system or it can be generated in situ. The catalyst is employed preferably in an amount within the range of 0.1 to 1.0 mol per 100 mols of the compound but larger amounts (up to 10 mol percent have been employed) may be used without detriment.

The catalytic reaction is carried out in the presence of an excess of a phosphine, such as triphenyl phosphine whereby the resulting catalytic system can be identified as in the examples as tetrakis-triphenyl phosphine palladium which may be represented by the formula (ph$_3$P)$_4$ Pd. In order to increase the catalytic lifetime, it is desirable to make use of an excess amount of phosphine such as from 0.5 to 10 mols extra phosphine per mol palladium.

As the phosphine, use can be made of any trivalent phosphorous compound. Thus, instead of triphenyl phosphine, use can be made of a trialkyl phosphine, a trialkyl phosphite such as trimethyl phosphite, a hexamethyl phosphorous triamine, or other polyphosphorous compound. The ratio of P/Pd° should be at least 4/1 and preferably 9-14/1.

Instead of the dimethyl sodiomalonate in Examples 1 and 2, others of the well known nucleophiles can be substituted for the dimethyl sodiomalonate or otherwise employed in the allylic alkylation reactions representative of the practice of this invention. Such nucleophiles can be classified as carbon nucleophiles i.e. stabilized carbanions represented by:

Malonate H$_1\overset{\ominus}{C}$(CO$_2$R)$_2$ acetoacetate H$_1\overset{\ominus}{C}$⟨COCH$_3$ / CO$_2$R⟩ sulfone esters H$\overset{\ominus}{C}$⟨SO$_2$PH / CO$_2$R⟩ phenyl thio esters H$\overset{\ominus}{C}$⟨Sph / C(=O)—CH$_3$⟩ and groups such as $\overset{\ominus}{C}$H(CN)$_2$, PhCH$\overset{\ominus}{C}$—$\overset{O}{\overset{\parallel}{C}}$—R In the above, the hydrogen group H can be replaced by an alkyl, aryl or vinyl group, or substituted alkyl, aryl or vinyl groups in which the alkyl group includes cycloalkyl and has from 1-18 carbon atoms, the aryl group includes alkaryl and may be represented by benzyl, naphthyl, anthracyl, phenyl, tolyl, pyrimidyl, pyridyl, pyrrole and heterocyclic groups and in which the substituent groups include hydroxy and halogen groups such as chloro, bromo, iodo and nitro and amino groups.

Each of the above nucleophiles are characterized by two stabilizing groups for the allylic alkylation reaction with retention of configuration for stereochemical control.

The carbon nucleophiles can be replaced with oxygen or nitrogen nucleophiles as by the replacement of carbanions with corresponding nitrogen and oxygen compounds.

Instead of tetrahydrofurane (THF), use can be made of other solvents compatible with the anion or nucleophile such as dimethyl sulfoxide (DMSO), various glymes which are alkylated ethylene/oxide polymers such as CH$_3$O(CH$_2$CH$_2$O)n CH$_3$, dipolar aprotic solvents such as acetonitrile, dimethyl formamide, hexamethylphosphoric triamide, and alcohols in which the nucleophile is soluble.

The allylic alkylation of this invention enables stereochemical reactions to be carried out on C-20 steroids to produce new and improved insecticidal and vitamin "D" compounds.

The allylic alkylation reaction of this invention is contra thermodynamics in that intermediates do not interconvert. For example:

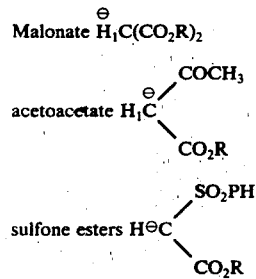

(thermodynamic complex) whereas in the reaction the intermediate is not the thermodynamically more stable and the complexes do not equilibrate. The stereochemistry of the alcohol, ester, or ether determines the stereochemistry of the proposed intermediate.

We claim:

1. The method in which an organic substrate having an OR group attached through the oxygen group to a carbon alpha to a double bond carbon in which OR is hydroxy, ether or ester group, comprising the displacement of the carbon-oxygen bond which is alpha to the double bond carbon and which connects to the oxygen group, with stereochemical control for retention of configuration by reacting the substrate with a nucleophile in the presence of a palladium (Pd°) catalyst, in which the nucleophile is selected from the group consisting of a carbon nucleophile in the form of carbanions stabilized with at least two stabilizing groups and a nitrogen nucleophile in which the carbanion is replaced with corresponding nitrogen compounds.

2. The method as claimed in claim 1 in which the palladium catalyst is present in an amount within the range of 0.1 to 2 mol percent of the compound containing the allylic carbon-oxygen bond.

3. The method as claimed in claim 1 in which the palladium catalyst includes a phosphine in an amount in excess of 4 mols of the phosphine per mol of palladium.

4. The method as claimed in claim 1 in which the palladium catalyst is employed in an amount up to 10 mol percent of the substrate.

5. The method as claimed in claim 1 in which the palladium catalyst is employed in an amount within the range of .1 to 1.0 mol per 100 mols of substrate.

6. The method as claimed in claim 1 which includes a phosphine in an amount of at least the ratio identified by the formula (Phosphine)$_4$Pd°.

7. The method as claimed in claim 6 in which the phosphine is present in an excess corresponding to 5 mols per mol of palladium.

8. The method as claimed in claim 6 in which the phosphine is selected from the group consisting of trialkyl phosphine, trialkyl phosphite, hexamethyl phosphorous triamine.

9. The method as claimed in claim 6 in which the phosphine is a polyphosphorous compound.

10. The method as claimed in claim 6 in which the phosphine is triphenyl phosphine.

11. The method as claimed in claim 10 in which the catalyst is tetrakis-triphenyl phosphine palladium.

12. The method in which an organic substrate having an OR group attached to a carbon alpha to a double bond C is substituted with a nucleophile with stereochemical control for retention of configuration by reaction of the substrate with the nucleophile in the presence of a Pd° catalyst in accordance with the equation

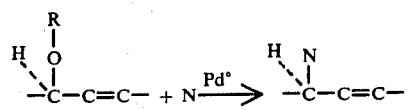

in which R is hydrogen or R' or OR' in which R' is an organic group and N is a nucleophile selected from the group consisting of a carbon nucleophile in the form of carbanions stabilized with at least two stabilizing groups and nitrogen nucleophiles in which the carbanions are replaced with corresponding nitrogen compounds.

13. The method as claimed in claim 12 in which the catalyst is a phosphine palladium catalyst in which the P/Pd ratio is 4/1 to 14/1.

14. The method as claimed in claim 1 in which the nucleophile is a carbon nucleophile selected from the group consisting of a malonate, acetoacetate, sulfone ester and phenyl thio ester.

15. The method as claimed in claim 1 in which the nucleophile is an organic compound having stabilized carbanions selected from the group consisting of

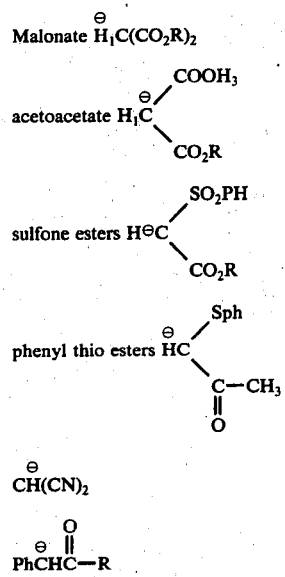

in which H can be replaced with a group consisting of alkyl, aryl, and vinyl and substituents thereof in which the alkyl group has from 1 to 18 carbon atoms, the aryl group is selected from the group consisting of benzyl, naphthyl, anthracyl, phenyl, tolyl, pyrimidyl, pyridyl, pyrrole and heterocyclic groups and in which the substituents are selected from the group consisting of hydroxy, chloro, bromo, iodo, nitro and amino groups.

* * * * *

UNITED STATES PATENT OFFICE
CERTIFICATE OF CORRECTION

Patent No. 4,051,157         Dated September 27, 1977

Inventor(s) Barry M. Trost et al.

It is certified that error appears in the above-identified patent and that said Letters Patent are hereby corrected as shown below:

Col. 1, line 45, change

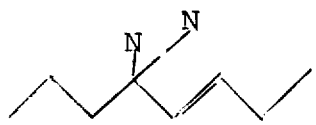

to:

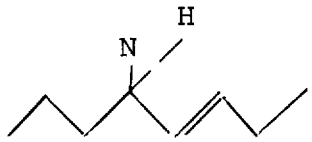

Signed and Sealed this

Fourteenth Day of March 1978

[SEAL]

Attest:

RUTH C. MASON
Attesting Officer

LUTRELLE F. PARKER
Acting Commissioner of Patents and Trademarks